United States Patent

Rose et al.

[11] Patent Number: 5,839,443
[45] Date of Patent: Nov. 24, 1998

[54] METHOD FOR INHIBITING THROMBOSIS IN A PATIENT WHOSE BLOOD IS SUBJECTED TO EXTRACORPOREAL CIRCULATION

[75] Inventors: Eric Rose, Tenafly, N.J.; David Stern, Great Neck, N.Y.; Ann Marie Schmidt, Franklin Lakes, N.J.; Talia Spanier, New York, N.Y.

[73] Assignee: The Trustees of Columbia University in the City of New York, New York, N.Y.

[21] Appl. No.: 648,561

[22] Filed: May 16, 1996

[51] Int. Cl.⁶ .................................................. A61B 19/00
[52] U.S. Cl. ............................................. 128/898; 435/13
[58] Field of Search .......................... 128/898; 530/384; 436/69; 435/183, 13; 604/49

[56] References Cited

U.S. PATENT DOCUMENTS

| 5,091,304 | 2/1992 | La Duca et al. | 435/13 |
| 5,169,786 | 12/1992 | Carroll et al. | 436/69 |
| 5,443,960 | 8/1995 | Dahlback | 435/13 |
| 5,472,850 | 12/1995 | Morrissey | 435/13 |
| 5,602,233 | 2/1997 | King | 530/381 |
| 5,618,788 | 4/1997 | Capon et al. | 514/12 |

OTHER PUBLICATIONS

Benedict, C.R., et al. (1994) "Endothelial-Dependent Procoagulant and Anticoagulant Mechanisms, Recent Advances in Understanding", Texas Heart Institute Journal 21: 86–90.

Kirchhofer, Daniel et al. (1995) "Active Site-Blocked Factors VIIa and Ixa Differentially Inhibit Fibrin Formation in a Human Ex Vivo Thrombosis Model," *Arterioscler. Thromb. Vasc. Biol.* 15: 1098–1106.

*Primary Examiner*—Mickey Yu
*Assistant Examiner*—Kelly O'Hara
*Attorney, Agent, or Firm*—John P. White; Cooper & Dunham LLP

[57] ABSTRACT

This invention provides an assay to monitor antithrombic activity of a Factor IXa compound infused into circulation of a patient which includes: (a) obtaining Factor IXa-deficient plasma; (b) mixing the plasma from step (a) with diatomaceous and with plasma from the patient; (c) incubating the mixture with a source of lipid and calcium chloride under conditions suitable for clot formation; and (d) measuring time necessary for clot formation in the incubate, thereby monitoring the antithrombic activity of the Factor IXa compound infused into the circulation of the patient.

10 Claims, 7 Drawing Sheets

METHOD FOR INHIBITING THROMBOSIS IN A PATIENT WHOSE BLOOD IS SUBJECTED TO EXTRACORPOREAL CIRCULATION

BACKGROUND OF THE INVENTION

Throughout this application, various publications are referenced by author and date. Full citations for these publications may be found listed alphabetically at the end of the specification immediately preceding the claims. The disclosures of these publications in their entireties are hereby incorporated by reference into this application in order to more fully describe the state of the art as known to those skilled therein as of the date of the invention described and claimed herein.

In cardiopulmonary bypass surgery, one of the critical requirements is the maintenance of blood fluidity and the absence of thrombosis. The cardiopulmonary bypass circuit presents a unique combination of factors favoring the development of a prothrombotic environment. The contact of blood with numerous devices which are associated with this procedure, such as membrane oxygenators and filters, has been implicated in the activation of the intrinsic (contact) pathway of coagulation. Since the bypass circuitry generates a highly-thrombogenic environment, high levels of anticoagulation therapies are required (Edmunds, 1995; Edmunds, 1993; Gravlee et al., 1990; Walenga et al., 1991; DeAnda et al., 1994; Brister et al., 1994; and Chomiak et al., 1993). Traditional intervention to prevent thrombosis in this setting has been the use of heparin. However, the use of heparin causes unacceptable side effects in certain patients. Such side effects may include the development of bleeding, heparin resistance or arterial/venous thrombosis. Despite investigations which have attempted to provide alternatives to the use of heparin, such as thrombin inhibitors (such as hirudin) and dermatan sulfate, no agent has yet been identified to replace or modify its use in clinical cardiac surgery (Walenga et al., 1991; DeAnda et al., 1994; Brister et al., 1994; and Chomiak et al., 1993).

SUMMARY OF THE INVENTION

This invention provides a method for inhibiting thrombosis in a patient whose blood is subjected to extracorporeal blood circulation which comprises contacting the extracorporeal circulating blood with a Factor IXa compound in an amount effective to inhibit thrombosis in the patient. The Factor IXa compound may include an active site-blocked Factor IXa compound or Glu-Gly-Arg chloromethyl ketone-inactivated human factor IXa compound. This invention also provides that the effective amount may be from about 0.1 $\mu$g/ml plasma to about 250 $\mu$g/ml plasma or from about 0.5 $\mu$g/ml plasma to about 25 $\mu$g/ml plasma. The patient may be subjected to extracorporeal blood circulation during transplant surgery or cardiopulmonary bypass surgery. This invention further provides for a pharmaceutical composition which includes an effective amount of a Factor IXa compound and a pharmaceutically acceptable carrier.

BRIEF DESCRIPTION OF THE FIGURES

Blood loss in the thoracic cavity was assessed in dogs treated with Factor IXai and dogs treated with heparin. After 1 hour of bypass followed by up to three hours of postoperative observation, blood loss was significantly less in the group receiving Factor IXai compared with the group receiving heparin (**, p<0.05).

FIGS. 3A, 3B, 3C, 3D, 3E, 3F 3G, and 3H. Histologic Examination of End Organs

Hematoxylin/eosin staining of heart, lung, kidney, and liver in dogs treated with Factor IXai are shown in FIGS. 3A, 3C, 3E, 3G.

A clotting assay was developed to rapidly and reproducibly assess the level of anticoagulation during cardiopulmonary bypass. As shown, this is an assay based on Factor IX deficient plasma and an optimized dose of cephalin to determine the functional anticoagulant effect of Factor IXai.

DETAILED DESCRIPTION OF THE INVENTION

This invention provides for a method for inhibiting thrombosis in a patient whose blood is subjected to extracorporeal blood circulation which includes contacting the extracorporeal circulating blood with a Factor IXa compound in an amount effective to inhibit thrombosis in the patient. The Factor IXa compound may include an active site-blocked Factor IXa compound or a Glu-Gly-Arg chloromethyl ketone-inactivated human factor IXa compound. The effective amount may include from about 0.1 $\mu$g/ml plasma to about 250 $\mu$g/ml plasma or from about 0.5 $\mu$g/ml plasma to about 25 $\mu$g/ml plasma or preferably from 0.7 $\mu$g/ml plasma to about 5 $\mu$g/ml plasma.

This invention further provides that the patient may be subjected to extracorporeal blood circulation during transplant surgery or cardiopulmonary bypass surgery. The patient may be subjected to extracorporeal blood circulation during any kind of cardiac surgery, including bypass grafting, valve replacement, congential repair heart surgery and heart transplantation. The patient may be a human being. The patient may also be subjected to extracorporeal life support. The patient may be a cardiogenic shock patient. The patient may be undergoing hemodialysis, continuous arteriovenous hemofiltration (CAVH), continuous veno-venous hemofiltration (CVVH), extracorporeal circulatory membrane oxygenation (ECMO), brain surgery, vascular surgery, abdominal surgery, orthopaedic surgery, hip replacement surgery, transplant surgery, or any surgery requiring cardiopulmonary bypass. The subject may be any patient requiring a mechanical circulatory assistance or ventricle assist device (i.e. LVAD). The subject may be a patient requiring new devices as described in Wickelgren, 1996 such as implantable defibrillators. The subject may also be a patient suffering with symptoms of systemic lupus erythematosus or TTP (thrombotic thrombocytopenic purpura). The subject may also be a patient requiring plasmapharesis.

One embodiment of the present invention is a pharmaceutical composition which may include an effective amount of a Factor IXa compound and a pharmaceutically acceptable carrier. The carrier may include a diluent. Further, the carrier may include an appropriate adjuvant, a herpes virus, a liposome, a microencapsule, a polymer encapsulated cell or a retroviral vector. The carrier may include an aerosol, intravenous, oral or topical carrier. The Factor IXa compound may be attached to a solid support. The Factor IXa compound may be linked to or bonded to tubing. The tubing may be part of an extracorporeal life support system.

As used herein "thrombosis" encompasses formation, development or presence of a blood clot or a blood coagulation which is located inside of a patient or inside of an extracorporeal life support system which circulates blood of the patient. Thrombosis also encompasses the presence of a thrombus which includes a blood clot occluding a blood vessel or formed in a heart cavity. Thrombosis also encompasses the activation of a plasmatic coagulation system in a patient which includes the production of cross-linked fibrin degradation product, protein C, free protein S, coagulation factor II, immunoglobulin G or albumin in the patient. "Thrombosis" also encompasses the formation of a white thrombus which may be composed of platelets and fibrin and is relatively poor in erythrocytes, a disseminated fibrin deposit thrombus or a red thrombus which may be composed of red cells and fibrin. Thrombosis may also include a thromboembolism which is the blocking of a blood vessel by a thrombus which may have been dislodged from a vein.

Thrombosis may occur in areas of retarded blood flow in the patient, at a site of injury or at an abnormal vessel wall in conjunction with an initiating platelet plug. Initiation of clot formation in response to tissue injury is carried out by the extrinsic pathway of clotting. Formation of a pure red thrombus in an area of restricted blood flow or in response to an abnormal vessel wall without tissue injury is carried out by the intrinsic pathway. Intrinsic and extrinsic pathways may converge in a final common pathway characterized by the activation of prothrombin to thrombin and the thrombin-catalyzed conversion of fibrinogen to the fibrin clot.

As used herein "a Factor IXa compound" may encompass the following: a Glu-Gly-Arg chloromethyl ketone-inactivated human factor IXa compound, an inactive Christmas factor, a plasma thromboplastin component, a Glu-Aly-Arg chloromethyl ketone-inactivated bovine factor IXa compound, a glutamyl-glycyl-arginyl-Factor IXa compound, a dansyl Glu-Gly-Arg chloromethyl ketone-inactivated bovine factor IXa (IXai), a Factor IXai, a competitive inhibitor of Factor IXa, a peptide mimetic of a Factor IXa compound, a carboxylated Christmas factor, a competitive inhibitor of prothrombinase complex, a des-γ-carboxyl Factor IX compound, a Factor IX compound lacking a calcium-dependent membrane binding function, an inactive Factor IX including only amino acids 1–47, an apoFactor IX compound including amino acids 1–47, Factor IX Bm Kiryu, a Val-313-to-Asp substitution in the catalytic domain of Factor IX, a Gly-311-to-Glu substitution in the catalytic domain of Factor IX, a Gly-311 to Arg-318 deletion mutant of Factor IX, an anti-Factor IXa antibody, an anti-Factor IXa monoclonal or polyclonal antibody. The Factor IXa compound may also include inactive species of Factor IX described in the references provided herein, especially Freedman et al., 1995; Furie and Furie, 1995; Miyata et al., 1994 and Wacey et al., 1994.

A Factor IXa compound may be an active site-blocked Factor IXa and be prepared as described in Experimental Details below. The Factor IXa compound may include a protein, a polypeptide or a peptide mimic. The compound may include at least the minimum number of domains necessary for activity. The domains may include a signal peptide, a propeptide, a Gla-domain rich in γ-carboxyglutamic acid residues, a short aromatic amino acid stack domain, two epidermal growth factor-like domains and a serine protease domain. The compound may include post-translational modifications including glycosylation, β-hydroxylation of aspartic acid, γ-carboxylation of glutamic acid and propeptide cleavage. The Factor IXa compound may be a concentrate obtained via heparin affinity chromatography or hydrophobic interaction chromatography. The Factor IXa compound may be a genetically engineered and expressed peptide. The Factor IXa compound may be a recombinant Factor IXa compound in which amino acids at the active site, especially at the active serine amino acid site, have been altered to render the recombinant Factor IXa functionally inactive, but still capable of competing with intact, native Factor IXa for cell surface binding.

Another embodiment of the present invention is an assay to monitor antithrombic activity of a Factor IXa compound infused into circulation of a patient which includes: (a) obtaining Factor IXa-deficient plasma; (b) mixing the plasma from step (a) with CELITE® and with plasma from the patient; (c) incubating the mixture with a source of lipid and calcium chloride under conditions suitable for clot formation; and (d) measuring time necessary for clot formation in the incubate, thereby monitoring the antithrombic activity of the Factor IXa compound infused into the circulation of the patient.

Another embodiment of the present invention is a method for evaluating the ability of an agent to inhibit an active site of a Factor IXa compound which includes: (a) contacting the Factor IXa compound with the agent to form a protein complex; (b) incubating the protein complex under conditions suitable for clot formation; (c) measuring time necessary for clot formation in the incubate, and (d) comparing the time measured in step (c) with the time measured in the absence of the agent, thus evaluating the ability of the agent to inhibit the active site of the Factor IXa compound.

Another embodiment of the present invention is an agent capable of inhibiting the active site of a Factor IXa compound obtained from the methods described herein. The agent may be a peptide, a peptidomimetic, a nucleic acid or a small molecule. The agent may be an antibody or portion thereof. The antibody may be a monoclonal antibody or a polyclonal antibody. The portion of the antibody may include a Fab.

The present invention provides for a method for inhibiting thrombosis in a patient whose blood is subjected to extracorporeal blood circulation which includes contacting the extracorporeal circulating blood with an agent capable of inhibiting a step in the intrinsic pathway of coagulation in an amount effective to inhibit thrombosis in the patient. The agent may be an active site-blocked Factor XII compound or an active site-blocked Factor XI compound.

One embodiment of the present invention is a peptidomimetic compound having the biological activity of a Factor IXa compound or a Glu-Gly-Arg chloromethyl ketone-inactivated human Factor IXa compound wherein the compound has a bond, a peptide backbone or an amino acid component replaced with a suitable mimic. Examples of unnatural amino acids which may be suitable amino acid mimics include β-alanine, L-α-amino butyric acid, L-γamino butyric acid, L-α-amino isobutyric acid, L-ϵ-amino caproic acid, 7-amino heptanoic acid, L-aspartic acid, L-glutamic acid, cysteine (acetamindomethyl), N-ϵ-Boc-N-α-CBZ-L-lysine, N-ϵ-Boc-N-α-Fmoc-L-lysine, L-methionine sulfone, L-norleucine, L-norvalin, N-α-Boc-NδCBZ-L-ornithine, N-δ-Boc-N-α-CBZ-L-ornithine, Boc-p-nitro-L-phenylalanine, Boc-hydroxyproline, Boc-L-thioproline. (Blondelle, et al. 1994; Pinilla, et al. 1995).

Also provided by the invention are pharmaceutical compositions comprising therapeutically effective amounts of polypeptide products of the invention together with suitable diluents, preservatives, solubilizers, emulsifiers, adjuvants and/or carriers. An "effective amount" as used herein refers to that amount which provides a therapeutic effect for a given condition and administration regimen. Such compositions are liquids or lyophilized or otherwise dried formulations and include diluents of various buffer content (e.g., Tris-HCl., acetate, phosphate), pH and ionic strength, additives such as albumin or gelatin to prevent absorption to surfaces, detergents (e.g., Tween 20, Tween 80, Pluronic F68, bile acid salts), solubilizing agents (e.g., glycerol, polyethylene glycerol), anti-oxidants (e.g., ascorbic acid, sodium metabisulfite), preservatives (e.g., Thimerosal, benzyl alcohol, parabens), bulking substances or tonicity modifiers (e.g., lactose, mannitol), covalent attachment of polymers such as polyethylene glycol to the protein, complexation with metal ions, or incorporation of the material into or onto particulate preparations of polymeric compounds such as polylactic acid, polyglycolic acid, hydrogels, etc, or onto liposomes, microemulsions, micelles, unilamellar or multilamellar vesicles, erythrocyte ghosts, or spheroplasts. Such compositions will influence the physical state, solubility, stability, rate of in vivo release, and rate of in vivo clearance. The choice of compositions will depend on the physical and chemical properties of the protein having the activity of a Factor IXa compound. For example, a product which includes a controlled or sustained release composition may include formulation in lipophilic depots (e.g., fatty acids, waxes, oils). Also comprehended by the invention are particulate compositions coated with polymers (e.g., poloxamers or poloxamines) and the compound coupled to antibodies directed against tissue-specific receptors, ligands or antigens or coupled to ligands of tissue-specific receptors. Other embodiments of the compositions of the invention incorporate particulate forms protective coatings, protease inhibitors or permeation enhancers for various routes of administration, including parenteral, pulmonary, nasal, oral, injection or infusion by intravenous, intraperitoneal, intracerebral, intramuscular, intraocular, intraarterial or intralesional.

The present invention incorporates U.S. Pat. Nos. 5,446,128, 5,422,426 and 5,440,013 in their entireties as references which disclose the synthesis of peptidomimetic compounds and methods related thereto. The compounds of the present invention may be synthesized using these methods. The present invention provides for peptidomimetic compounds which have substantially the same three-dimensional structure as those compounds described herein.

In addition to the compounds disclosed herein having naturally-occurring amino acids with peptide or unnatural linkages, the present invention also provides for other structurally similar compounds'such as polypeptide analogs with unnatural amino acids in the compound. Such compounds may be readily synthesized on a peptide synthesizer available from vendors such as Applied Biosystems, Dupont and Millipore.

As used herein, the term "pharmaceutically acceptable carrier" encompasses any of the standard pharmaceutically accepted carriers, such as phosphate buffered saline solution, water, emulsions such as an oil/water emulsion or a triglyceride emulsion, various types of wetting agents, tablets, coated tablets and capsules. An example of an acceptable triglyceride emulsion useful in intravenous and intraperitoneal administration of the compounds is the triglyceride emulsion commercially known as Intralipid®.

Typically such carriers contain excipients such as starch, milk, sugar, certain types of clay, gelatin, stearic acid, talc, vegetable fats or oils, gums, glycols, or other known excipients. Such carriers may also include flavor and color additives or other ingredients.

When administered, compounds are often cleared rapidly from the circulation and may therefore elicit relatively short-lived pharmacological activity. Consequently, frequent injections of relatively large doses of bioactive compounds may by required to sustain therapeutic efficacy. Compounds modified by the covalent attachment of water-soluble polymers such as polyethylene glycol, copolymers of polyethylene glycol and polypropylene glycol, carboxymethyl cellulose, dextran, polyvinyl alcohol, polyvinylpyrrolidone or polyproline are known to exhibit substantially longer half-lives in blood following intravenous injection than do the corresponding unmodified compounds (Abuchowski et al., 1981; Newmark et al., 1982; and Katre et al., 1987). Such modifications may also increase the compound's solubility in aqueous solution, eliminate aggregation, enhance the physical and chemical stability of the compound, and greatly reduce the immunogenicity and reactivity of the compound. As a result, the desired in vivo biological activity may be achieved by the administration of such polymer-compound adducts less frequently or in lower doses than with the unmodified compound.

Attachment of polyethylene glycol (PEG) to compounds is particularly useful because PEG has very low toxicity in mammals (Carpenter et al., 1971). For example, a PEG adduct of adenosine deaminase was approved in the United States for use in humans for the treatment of severe combined immunodeficiency syndrome. A second advantage afforded by the conjugation of PEG is that of effectively reducing the immunogenicity and antigenicity of heterologous compounds. For example, a PEG adduct of a human protein might be useful for the treatment of disease in other mammalian species without the risk of triggering a severe immune response. The compound of the present invention capable of alleviating symptoms of a cognitive disorder of memory or learning may be delivered in a microencapsulation device so as to reduce or prevent an host immune response against the compound or against cells which may produce the compound. The compound of the present invention may also be delivered microencapsulated in a membrane, such as a liposome.

Polymers such as PEG may be conveniently attached to one or more reactive amino acid residues in a protein such as the alpha-amino group of the amino terminal amino acid, the epsilon amino groups of lysine side chains, the sulfhydryl groups of cysteine side chains, the carboxyl groups of aspartyl and glutamyl side chains, the alpha-carboxyl group of the carboxy-terminal amino acid, tyrosine side chains, or to activated derivatives of glycosyl chains attached to certain asparagine, serine or threonine residues.

Numerous activated forms of PEG suitable for direct reaction with proteins have been described. Useful PEG reagents for reaction with protein amino groups include active esters of carboxylic acid or carbonate derivatives, particularly those in which the leaving groups are N-hydroxysuccinimide, p-nitrophenol, imidazole or 1-hydroxy-2-nitrobenzene-4-sulfonate. PEG derivatives containing maleimido or haloacetyl groups are useful reagents for the modification of protein free sulfhydryl groups. Likewise, PEG reagents containing amino hydrazine or hydrazide groups are useful for reaction with aldehydes generated by periodate oxidation of carbohydrate groups in proteins.

This invention is illustrated in the Experimental Detail section which follows. These sections are set forth to aid in an understanding of the invention but are not intended to, and should not be construed to, limit in any way the invention as set forth in the claims which follow thereafter.

EXPERIMENTAL DETAILS

Selective inhibition of the intrinsic pathway of coagulation is one possible way to avoid the use of heparin in extracorporeal circulation. Leaving intact the tissue factor-mediated extrinsic pathway of coagulation (initiated by tissue factor-VIIa) may obviate both adverse bleeding and potential prothrombotic side effects of heparin. These side effects are found in certain sensitized patients such as patients with heparin-induced thrombocytopenia. In these cases, heparin may be associated with a prothrombic situation.

The coagulation Factor IX/IXa is a single chain vitamin K-dependent coagulation protein. Limited proteolysis of Factor IX results in a cleavage product which is a two-chain serine protease, Factor IXa, which requires association with the cell surface and the cofactor VIIIa in order to express and exhibit procoagulant activity (Gurewich et al., 1979; Gitel et al., 1977; and Benedict et al., 1991). Factor IXa has an important role in coagulation. When clotting is triggered in the intravascular space, (i.e., thrombosis), it is initiated in the presence of low amounts of tissue factor. In this case, Factor IX becomes preferentially activated to Factor IXa, which then feeds into the rest of the procoagulant cascade, leading to fibrin formation. In contrast, activation of Factor X by tissue factor is less favored by at least an order of magnitude under these conditions. Extravascular coagulation, especially protective hemostasis, occurs in the presence of large amounts of tissue factor on mesenchymal cells and the role of Factor IXa is much less important when direct activation of Factor X occurs. Factor IXa is essentially bypassed. Thus, it may be hypothesized that inhibition of Factor IXa participation in coagulation could provide a selective means of anticoagulation by inhibiting intravascular thrombosis without impairing extravascular hemostasis.

Studies have shown rapid clearance of Factor IX from the intravascular space, the association of infused and endogenous Factor IX with the vessel wall (Thompson, 1986 and Stern et al., 1987) and in vitro studies have demonstrated Factor IX binding to endothelium and platelets. (Heimark and Schwartz, 1983; Stern et al., 1983; and Ahmad et al., 1989) Studies have been performed to characterize the molecular basis of this coagulation protein-cell surface interaction. At the level of the ligand, the amino-terminal gamma-carboxyglutamic acid-containing domain of Factor IX has been shown to be essential for cell surface binding (Toomey et al., 1992; Astermark et al., 1991; Derian et al., 1989; and Ryan et al., 1989). At the level of the cell surface site, previous studies have demonstrated that Factor IX binding involves a protease-sensitive polypeptide. This polypeptide in endothelial cell studies appears to have an Mr~150 kDa (Rimon et al., 1987) and on platelets appears to have an Mr~250 kDa (London and Walsh, 1992).

Factor IXa may be capable of binding to cellular interaction sites in the vessel wall. It is possible that such sites may be a target for therapeutic intervention in certain thrombotic disorders such as cardiopulmonary bypass.

Studies have demonstrated that Factor IX/IXa may contribute to thrombosis. It was found that Factor IXa resulted in formation of thrombi (Gurewich et al., 1979) and that Factor IXa has potent thrombogenic properties in the Wessler stasis model of thrombosis (Gitel et al., 1977). Factor IXa participates in procoagulant pathways as a component of the Factor IXa-VIIIa-X activation complex (intrinsic pathway of coagulation). Multiple studies in vitro demonstrated that use of active site-blocked IXa (dansyl-glutamyl-glycyl-arginyl Factor IXa, or IXai) prevented the assembly of IXa into this critical complex (Chomiak et al., 1993; Thompson, 1986; Lollar and Fass, 1984; Stern et al., 1985; and Ahmad et al., 1989). Studies have demonstrated the functionally-active site of Factor IXa (Astermark et al., 1992 and Ahmad et al., 1992). A role for active site-blocked Factor IXa (Factor IXai) has been demonstrated in preventing coronary artery thrombosis in a canine model in which thrombosis is initiated by the introduction of electric current. Extravascular hemostasis was secured, as no untoward bleeding was detectable in an incisional wound model (Benedict et al., 1991). Therefore, Factor IXai may be an ideal antithrombotic agent for use in cardiopulmonary bypass surgery. Specifically, the extrinsic pathway of coagulation would be unaffected and thus the patient would not be predisposed to excess bleeding. Furthermore, other limiting side effects of heparin would be precluded.

In the studies described below, active site-blocked Factor IXa is shown to be a safe and effective antithrombotic agent in a canine model of coronary artery bypass and surgery. An aortotomy was performed in order to stimulate typical cardiac procedures. Pathways regulating control extravascular hemostasis appeared intact because significantly less bleeding was noted in dogs treated with Factor IXai compared with dogs treated with heparin. Furthermore, model studies of cardiopulmonary bypass utilizing active site-blocked Factor IXa further support the efficacy and safety of the present invention.

MATERIALS AND METHODS

Factor IX/IXa was purified from human plasma according to previously-published methods (Benedict et al., 1991 and Stern et al., 1987) and inactivated using glu-gly-arg-chloromethylketone as described (Benedict et al., 1991 and Lollar and Fass, 1984). Purity of the reagents was then ascertained using SDS-PAGE and standard clotting assays (Benedict et al., 1991 and Lollar and Fass, 1984).

Animal studies

Cardiopulmonary bypass in dogs (each dog weighing approximately 15 kgs) and baboons (each baboon weighing approximately 11 kgs) (Daly et al., 1988 and Bernabei et al., 1995) was instituted and maintained for one hour with cooling to 32° C. An aortotomy was performed in order to simulate cardiac surgery procedures. Animals were then weaned from bypass and blood loss was monitored for up to 3 hours.

Animals received either heparin (at a standard dose of 300 IU/kg and protamine (2 mg/kg) reversal) or active site-blocked Factor IXa (at different doses as indicated below).

Multiple parameters were assessed in all animals (receiving either heparin or Factor IXai) as follows:
1. In order to test for evidence of fibrin deposition in the bypass circuitry, the cardiopulmonary bypass tubing and filters were removed at the end of bypass and subjected to analysis by scanning electron microscopy in order to detect possible evidence of fibrin deposition.
2. After sacrifice of the dogs or the baboons, necropsy was performed and the heart, lungs, liver and kidneys were removed. These organs were fixed in formalin and examined by Hemotoxylin & Eosin staining and immunofluorescence for evidence of clot formation or fibrin deposition as well as for the presence of microemboli.
3. Routine hematologic analysis was performed prior to initiation of cardiopulmonary bypass and at every 30 minute interval during the cardiopulmonary bypass in order to determine hemoglobin levels, hematocrit levels, levels of platelets and fibrinogen, white blood cell count, prothrombin time, activated partial thromboplastin time and activated clotting time.
4. Continuous hemodynamic measurements were performed prior to, during and for up to 3 hours after the institution of cardiopulmonary bypass.
5. Blood loss was quantitated in the thoracic cavity by collecting all blood in the area during the cardiopulmonary bypass itself and for up to three hours after completion of cardiopulmonary bypass.
6. The extent of activation of coagulation in this model was determined in order to determine the contribution of thrombin generation and fibrinolysis, which occurs in the setting of treatment with heparin, and the contribution of Factor IXai to coagulation. For the canine studies, measurement of thrombin-anti-thrombin complex (or TAT, commercially available from Behring Diagnostics, Boston Mass.) was utilized as a measure of thrombin generation. This assay was cross-reactive with dog plasma. TAT was measured in animals/group of heparin or Factor IX-ai treated dogs prior to institution of cardiopulmonary bypass/IXai treatment and every 30 minutes during cardiopulmonary bypass and every 60 minutes after cardiopulmonary bypass terminated until the animal was sacrificed at 3 hours. In baboon studies, TAT was measured as described herein and prothrombin fragment 1+2($F_{1+2}$; Behring Diagnostics) was measured. This assay cross-reacts with standards obtained from human plasma.
7. Markers of fibrinolysis were assessed to identify the extent to which excess fibrinolysis generated during treatment with heparin likely contributed to increased bleeding. These parameters were directly compared with those obtained in dogs treated with Factor IXai. Levels of d-dimers were assessed at the same time points measured for TAT.

RESULTS

EXAMPLE 1

Canine model of cardiopulmonary bypass

Four dogs were treated with standard doses of heparin (300 IU/kg followed by protamine 2 mg/kg) and five dogs were treated with Factor IXai. In dogs (3 total) treated with 460 μg/kg (single intravenous infusion just prior to the initiation of cardiopulmonary bypass), there was no evidence of excess pressure in the cardiopulmonary bypass circuit or gross clot formation in the tubing. These results were similar to those observed in the dogs treated with heparin. Similarly, systemic hemodynamic profiles were similar in both groups throughout the procedure suggestive of the absence of clinically-relevant thromboses within the bypass circuitry.

Figure 1:
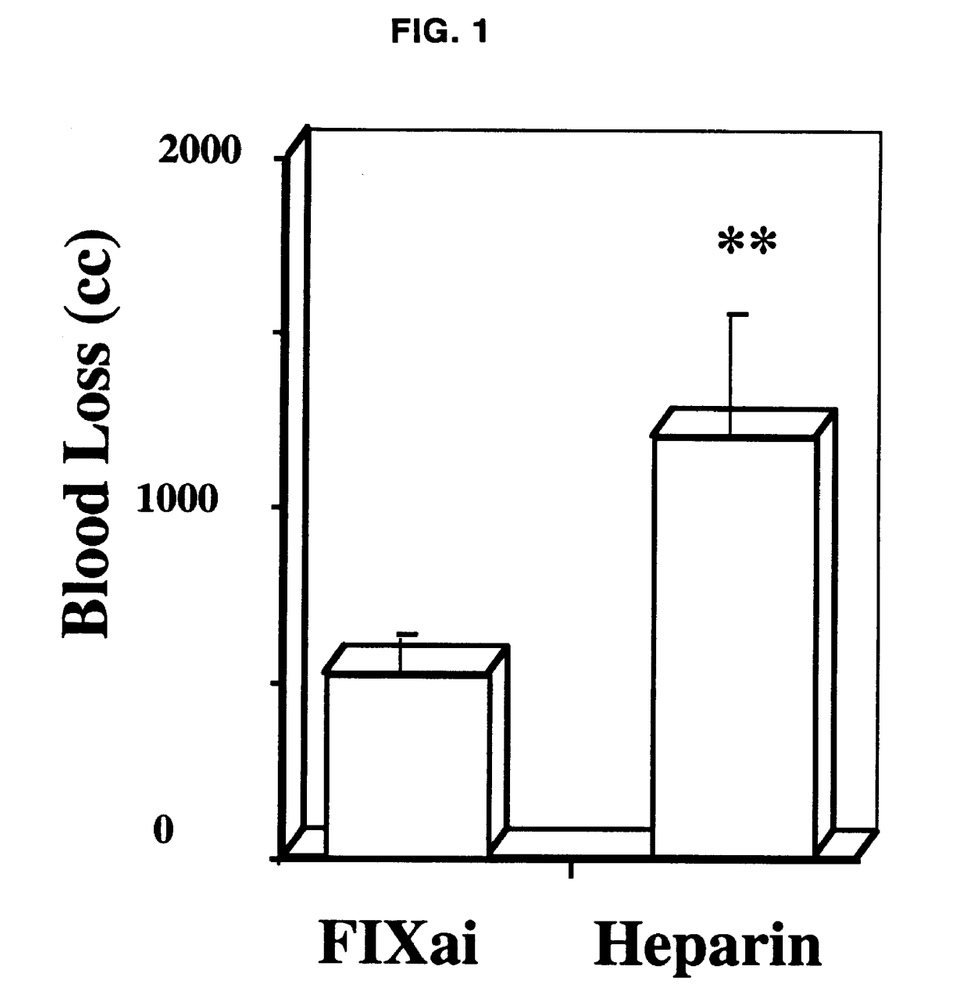
FIG. 1. Blood Loss: Factor IXai vs Heparin
Figure 2A:
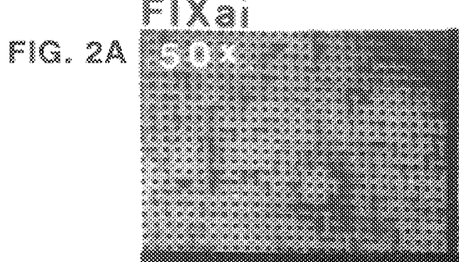
FIGS. 2A, 2B, 2C, 2D, 2E and 2F. Scanning Electron Microscopic Analysis of Arterial Filter in Factor IXai vs Heparin Scanning electron microscopic analysis of the arterial filters is depicted. The FIGS. 2A, 2C and 2E show serial magnification of the arterial filters in Factor IXai treated dogs (50×(top), 200× (middle), 2000× (bottom)). The FIGS. 2B, 2D and 2F show similar views of the heparin treated dogs. As demonstrated in these pictures, cardiopulmonary bypass performed with Factor IXai was associated with similar amounts of clinically inapparent fibrin deposition compared with the use of traditional heparin.
Figure 2B:
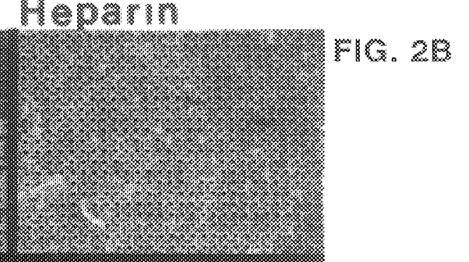
Figure 2C:
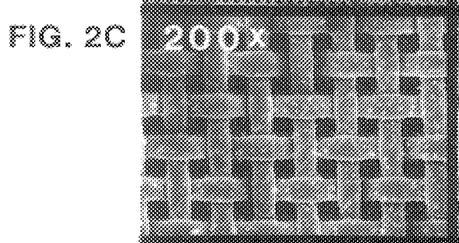
Figure 2D:
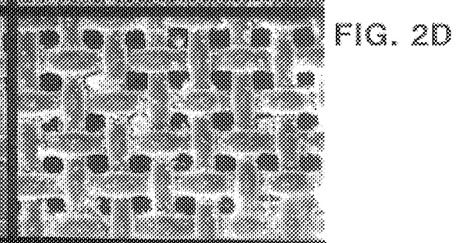
Figure 2E:
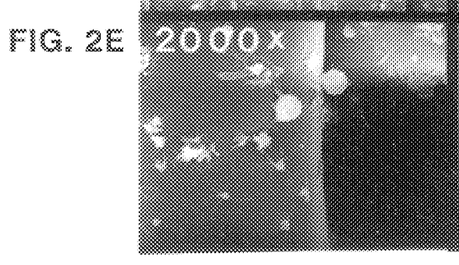
Figure 2F:
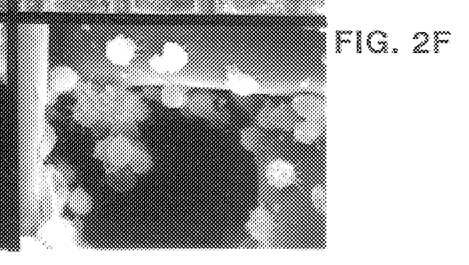
Figure 3A:
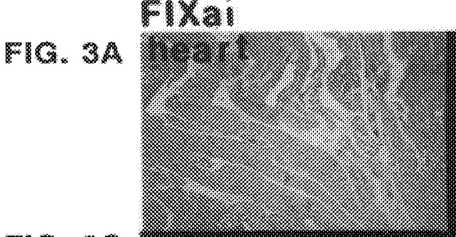
Figure 3B:
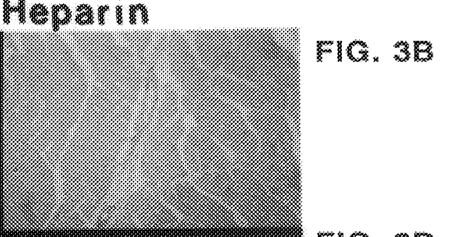
FIGS. 3B, 3D, 3F and 3H show samples evaluated in dogs treated with heparin. These studies reveal the absence of fibrin deposition and micro emboli in both groups.
Figure 3C:
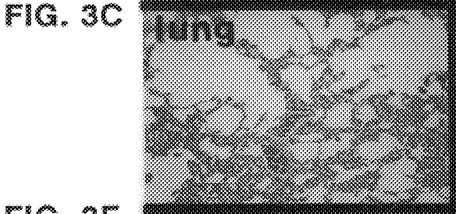
Figure 3D:
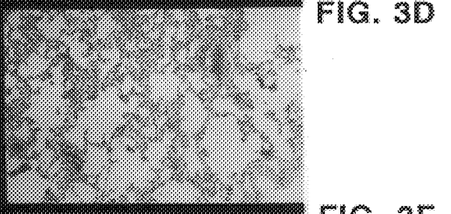
Figure 3E:
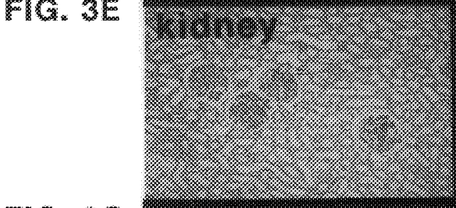
Figure 3F:
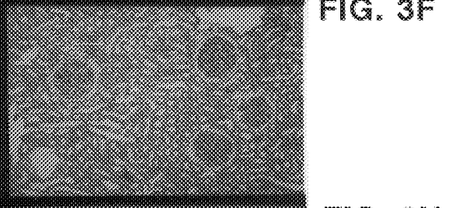
Figure 3G:
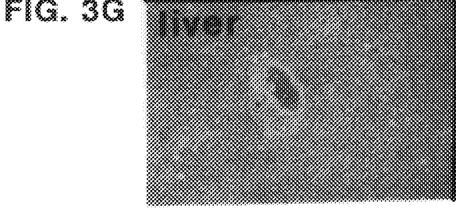
Figure 3H:
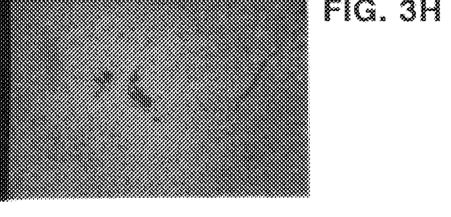
Figure 4A:
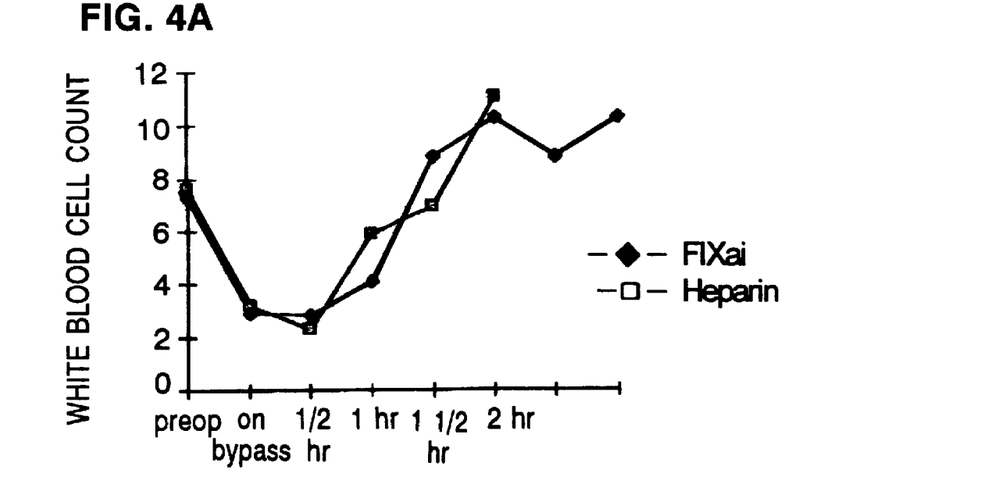
FIGS. 4A, 4B, 4C. 4D and 4E. Analysis of Blood Samples in Dogs Treated with Factor IXai and Heparin Blood samples were drawn at intervals throughout the surgical procedure and evaluated. Similar dilutional decreases in white blood cells, hematocrit, and platelet count were observed in each group. Levels of prothrombin time and partial thromboplastin time remained baseline in Factor IXai treated dogs while there was significant elevation in dogs anticoagulated with heparin. (**p<0.05) {closed diamonds represent Factor IXai; open squares represent heparin}.
Figure 4B:
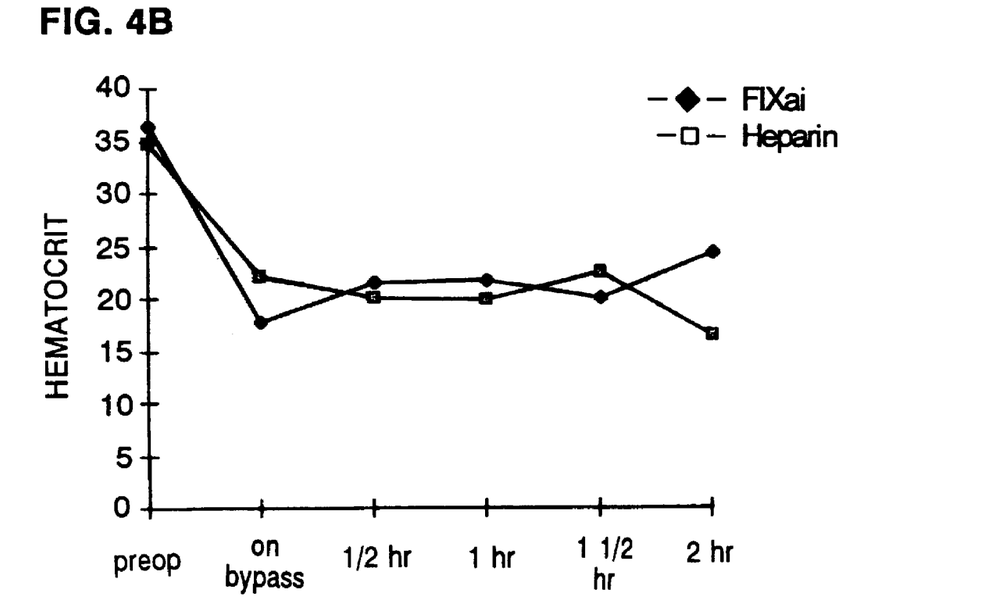
Figure 4C:
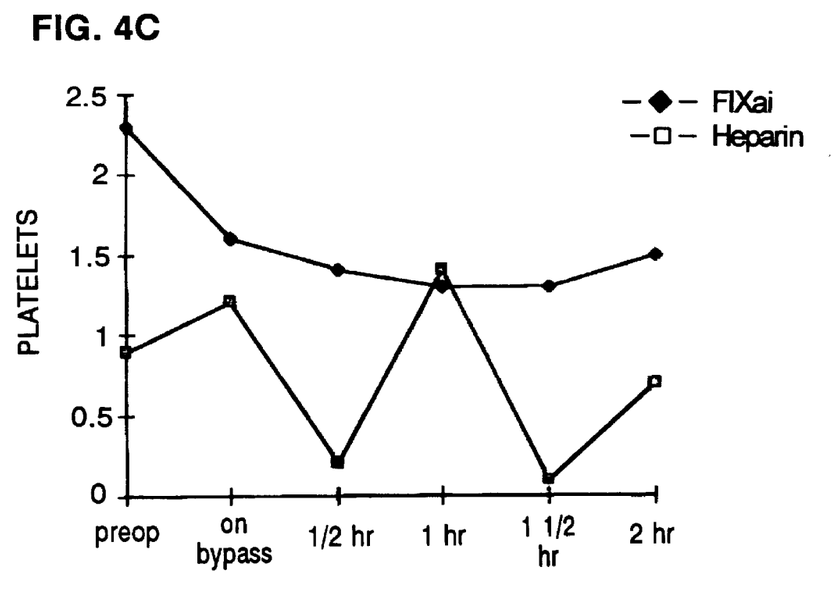
Figure 4D:
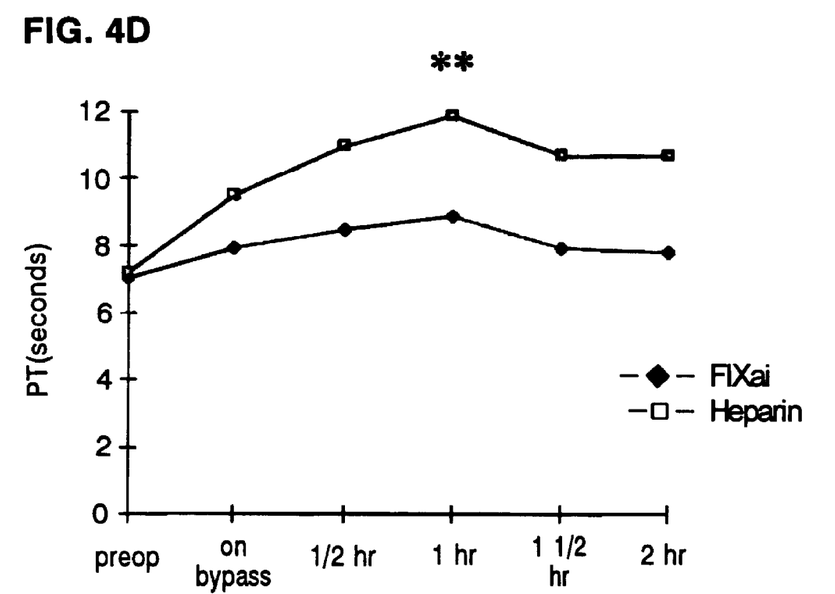
Figure 4E:
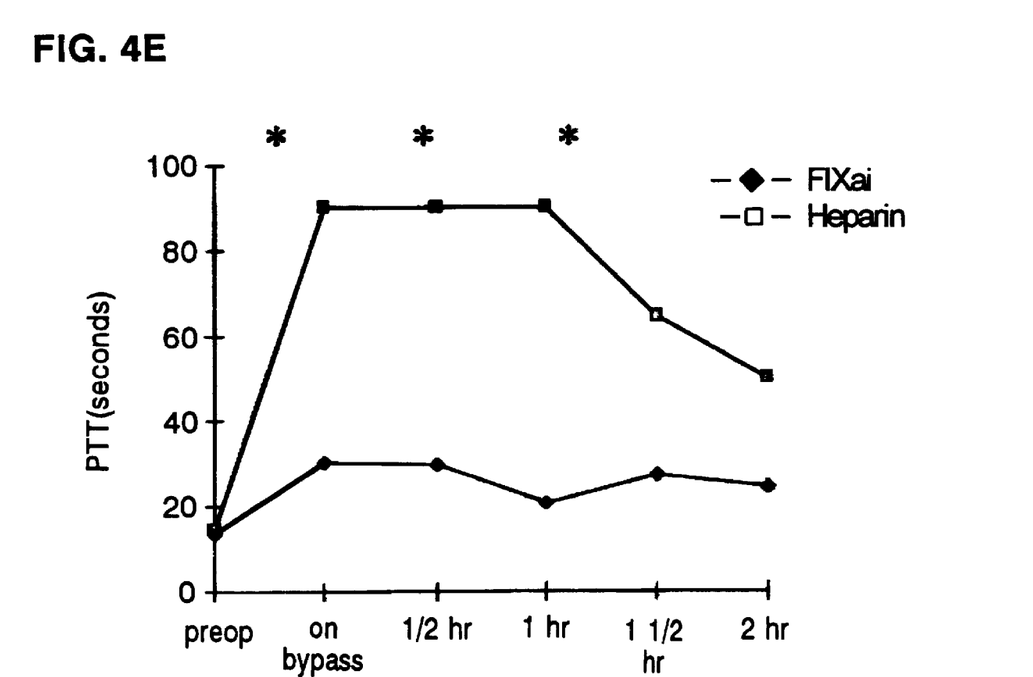

Blood loss in the thoracic cavity was significantly less in the group receiving Factor IXai compared with the dogs receiving heparin (FIG. 1). After four hours of observation (one hour during cardiopulmonary bypass itself) and three hours following the termination of cardiopulmonary bypass, dogs receiving Factor IXai accumulated 600 ml of blood within the thoracic cavity. This was in marked contrast to dogs receiving standard doses of heparin in which 1000 ml of blood was quantitated in the thoracic cavity ($p<0.01$).

Consistent with these data and the hypothesis that selective inhibition of the intrinsic pathway of coagulation would leave unaffected the tissue factor-mediated extrinsic pathway of coagulation, dogs that received Factor IXai were observed to have hemostatic clot along the cut surface of the sternum and in surgical tissue planes. However, the dogs treated with heparin did not have these hemostatic markers.

In order to detect pathological quantities of deposited fibrin within the bypass circuits, the tubing and filters were immediately removed after cardiopulmonary bypass and analyzed by scanning electron microscopy. As shown in FIG. 2, cardiopulmonary bypass performed with Factor IXai resulted in similar amounts of fibrin deposition (left panel) compared with cardiopulmonary bypass performed with the use of traditional heparin (opposite). The amount of fibrin deposition in both cases was clinically-inapparent.

In addition to microscopic examination of the bypass material, organs removed at necropsy were examined by microscopy with Hematoxylin/eosin staining. These studies revealed the absence of fibrin deposition and microemboli in the liver, lungs, kidneys and myocardium as shown in FIG. 3.

Analysis of blood samples revealed similar dilutional decreases in hematocrit, platelet count and fibrinogen levels in both groups of animals treated with either Factor IXai or heparin (FIG. 4).

As demonstrated in FIG. 4, Prothrombin time (PT) remained at about the level of the control in the Factor IXai-treated group (7.9+0.1 sec) and activated Partial thromboplastin time (PTT) was mildly elevated (30.4±11 secs). As expected, heparin-treated dogs had significant elevation of PT and PTT (11.9±0.6 secs and >90 secs, respectively). ACT (Activated clotting time) used in cardiopulmonary bypass to quickly assess the level of anticoagulation with heparin (ideal>480 secs in human subjects) was >400 secs in the heparin-treated group, but unchanged in the Factor IXai-treated group.

In order to determine the optimal dose of Factor IXai that was necessary to safely prevent thrombosis while securing extravascular hemostasis, different doses of Factor IXai were utilized in the canine model. These data revealed that a dose of 600 μg/kg (one dog) produced no evidence of clotting in the bypass circuitry. However, there was evidence of increased bleeding in this group (900 ml of blood in dogs treated with Factor IXai) compared with dogs that received a lower dose (460 μg/kg) of Factor IXai. A third group of dogs (1100 ml of blood in dogs) treated with heparin also had evidence of increased bleeding. These data suggested that the 600 μg/ml dose of Factor IXai was excessive since the lower dose (at least 460 μg ) was successful.

In order to determine the minimal dose of Factor IXai needed to prevent clotting in the bypass circuitry, one dog was treated with Factor IXai at a dose of 300 µg/kg. This experiment demonstrated that there was no evidence of improper clotting of the bypass circuitry. In addition, blood loss in the thoracic cavity was 600 ml of blood compared with 1100 ml of blood in the thoracic cavity of dogs treated with standard doses of heparin.

Figure 5A:
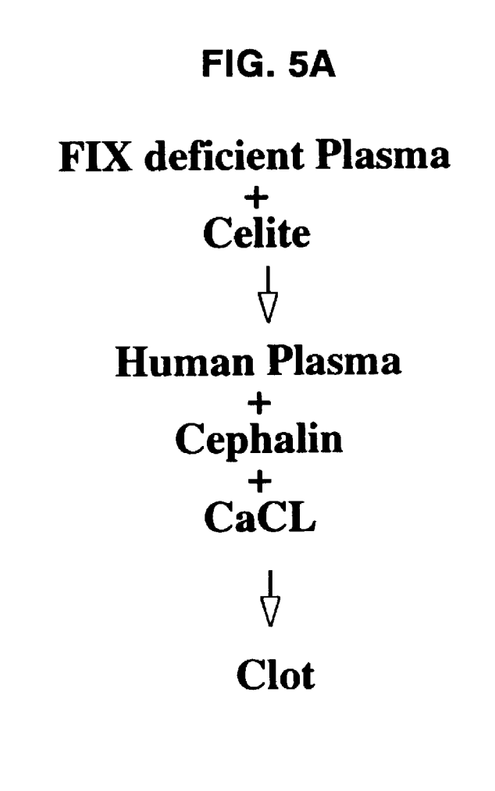
FIGS. 5A and 5B. Factor IX based Clotting Assay.
Figure 5B:
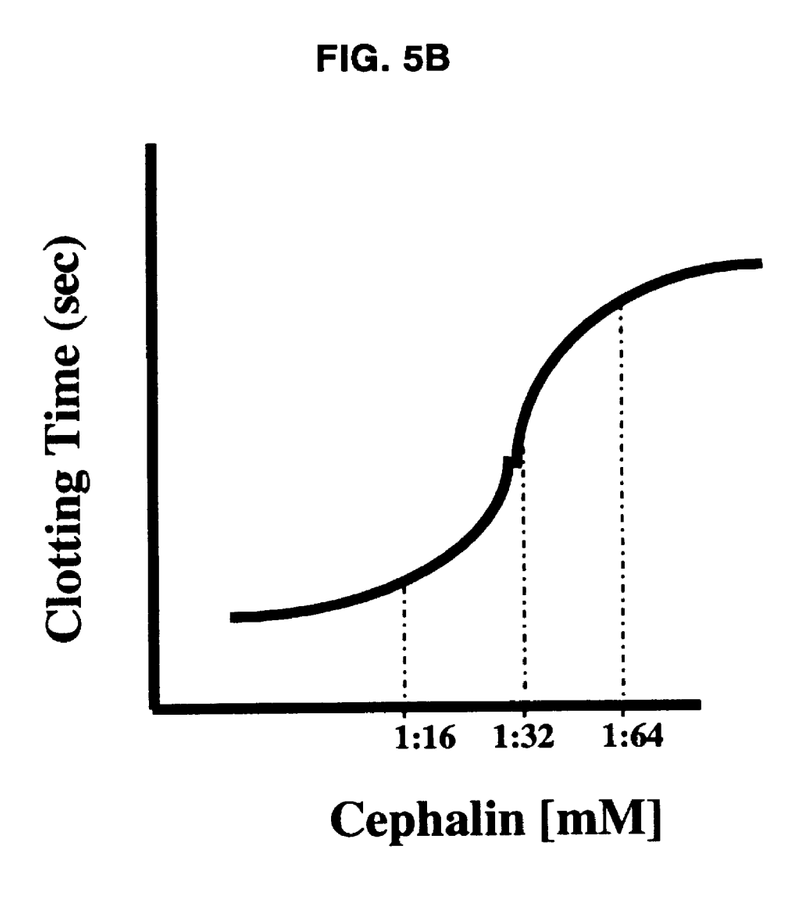

As indicated above, there was an inability to assess the effectiveness of anticoagulation via measurement of activated clotting time in dogs treated with Factor IXa. Thus, a clotting assay was developed in order to determine the functional effectiveness of Factor IXai rapidly and reproducibly, thereby providing a means to assess the level of anticoagulation frequently during cardiopulmonary bypass. It is necessary to be able to frequently determine the ability of blood of a human patient to coagulate throughout the performance of cardiopulmonary bypass surgery or any majory surgery. The sensitivity of the assay was dependent on the use of Factor IX-deficient plasma and an optimized dose of cephalin (source of phospholipid) as shown in FIG. 5. Comparison of plasma from dogs treated with Factor IXai compared with control dog plasma revealed a four-fold increase in clotting time. This assay therefore provided a means of rapidly determining the extent of anticoagulation in animals treated with Factor IXai. Further studies may be performed to determine the desired extent of increased clotting time in this assay in order to achieve maximal antithrombotic effects, while maintaining intact the pathways of extravascular hemostasis.

EXAMPLE 2

Baboon model of cardiopulmonary bypass

Studies in baboon models of cardiopulmonary bypass are effective and predictive for future testing of active site-blocked Factor IXa in human subjects. Adequate pre-clinical data in primates is expected to more closely predict expected results in humans. Experiments have been performed in baboons. In one experiment, a baboon received Factor IXai (460 µg/kg) and a second baboon received heparin/protamine (300 IU/heparin followed by protamine [2 mg/kg]). The data from these trials revealed that there was no evidence of pathologic clotting in the bypass circuitry observed in either group of animals. Similar to the results from the case of dogs treated with Factor IXai, there was evidence of significantly decreased blood loss in the thoracic cavity of baboons treated with Factor IXa (320 ml of blood) compared with baboons treated with standard doses of heparin (600 ml of blood).

Preliminary hematologic analysis in the baboons shows that there are similar dilutional decreases in hematocrit, white blood cell counts and platelets as seen in the dog trials. Other studies were completed to investigate the effects of Factor IXai in baboons and to characterize the hemostatic findings.

DISCUSSION

The use of heparin has been associated with multiple side effects in certain patients undergoing cardiopulmonary bypass. The side effects include excessive bleeding (at least in part due to excess fibrinolysis), heparin resistance (potentially requiring use of anti-thrombin III to achieve desire heparin effects), heparin-induced thrombocytopenia (with potential for either excess bleeding or clotting in the arterial and/or venous system) and need for reversal with protamine.

Data from studies of the canine and baboon models of cardiopulmonary bypass suggest that in patients in whom heparin is relatively contraindicated, the use of active site-blocked Factor IXai as an antithrombotic agent may be useful to prevent pathologic clotting in the circuitry. This clotting may be lessened by the inhibition of the intrinsic pathway of coagulation. However, securing the functional responsiveness of the extrinsic (extravascular) pathway of coagulation is critical in minimizing excess blood loss due to cut vessels of the sternum, etc. Furthermore, obviating the use of heparin will be useful to minimize the excessive fibrinolysis generated by its use at doses required to maintain an activated clotting time>480 secs during cardiopulmonary bypass.

The use of Factor IXai has been shown to be a safe means of inhibition of thrombosis during cardiopulmonary bypass and a range of other cardiac and surgical procedures.

In canine and baboon cardiopulmonary bypass models, the selective inhibition of the intrinsic/contact system of coagulation has been demonstrated. Maintenance of the extrinsic/tissue factor mediated pathway allows for the successful maintenance of patency of the cardiopulmonary bypass circuit while allowing extravascular hemostasis. The possible applications of this therapeutic intervention extend well beyond the cardiopulmonary bypass setting.

For example, extracorporeal life support with extracorporeal membrane oxygenation (ECMO) (Magovern, 1995) is being used more frequently to support adult patients who develop cardiogenic shock. Studies have demonstrated that this intervention provides excellent oxygenation and hemodynamic support in this critically ill population. However, the morbidity and mortality associated with this procedure remains high. Central to the life-threatening complications associated with extracorporeal membrane oxygenation is the unavoidable need for systemic heparinization with its attendant hemorrhagic complications (Muehrcke et al., 1995). Heparin-bonded circuits have provided an alternative to full heparinization with some success, but this model still carries the significant risk of bleeding and thrombosis (Perchinisky et al., 1995 and Atkinson et al., 1992). Selective intravascular anticoagulation with Factor IXai would logically be an ideal alternative to traditional heparinization.

Baboons may be maintained on an extracorporeal membrane oxygenation circuit for up to one week with anticoagulation initiated by Factor IXai, in lieu of heparin. Similarly, active site-blocked Factor IXa may also be useful in any setting requiring the contact of blood with extracorporeal circuitry, such as plasmapheresis, renal hemodialysis, continuous anterio-venus hemofiltration (CAVH), venovenus hemofiltration (CVVH), extracorporeal circulatory membrane oxygenation (ECMO), brain surgery, vascular surgery, abdominal surgery, transplant surgery, any procedure in which systemic anticoagulation is routinely required, and any procedure in which a patient requires a mechanical circulatory assistance, ventricle assist device, artificial heart, left/right ventricle assist device or a similar biomedical device.

Another potential indication for the use of active site-blocked Factor IXa as an anticoagulant involves the surgical intervention of intracranial aneurysms. Surgery for aneurysm correction must be performed without the use of systematic anticoagulation because the risk of hemorrhagic complications associated with the use of heparin during this procedure are unacceptable. A "watershed" portion of the brain matter immediately adjacent to the aneurysm is therefore sacrificed with the surgical clipping of the aneurysm as tributary vessels thrombose and thus infarct adjacent brain tissue. This procedure may be performed with local infusion of Factor IXai to allow intravascular anticoagulation, thus maintaining blood flow through tributaries of the clipped vessel to the brain matter around the aneurysm. Meanwhile, extravascular/tissue factor mediated hemostasis would ensure that a hemorrhagic infarction did not occur. A murine model of stroke may be studied to determine if local infusion of Factor IXai will limit the "watershed" region around a clipped cerebral vessel while preventing hemorrhage.

References

Ahmad, S., Rawala-Sheikh, R., Ashby, B. And P. Walsh (1989) Platelet receptor-mediated Factor X activation by Factor Ixa: high affinity Factor IX receptors induced by Factor VIII are deficient on platelets in Scott syndrome. *J. Clin. Invest.* 84:824–828.

Ahmad, s., Rawala-Sheikh, R. and Walsh, P. Comparative interactions of factor IX and Ixa with human platelets. (1989) *J. Biol. Chem.* 264:3244–3251.

Ahmad, S. D., Rawala-Sheikh, R., Cheung, W. F., Stafford, D. W., Walsh, P. N. (1992) The role of the first growth factor domain of human factor Ixa in binding to platelets and in factor X activation. *J. Biol. Chem.* 267(12):8571–6.

Astermark, J., Bjork, I., Ohlin, A., Stenflo J. (1991) Structural requirements for Ca++ binding to gamma carboxy glutamic acid and epidermal growth factor like regions of FIXa studies using intact domains isolated from controlled proteolytic digests of bovine Factor Ixa. *J. Biol. Chem.* 266:2430–2437.

Astermark, J., Hogg, P. J., Bjork, I., Stenflo, J. (1992) Effects of gamma-carboxyglutamic acid and epidermal growth factor-like modules of factor IX on Factor activation. Studies using proteolytic fragments of bovine factor IX. *J. Of Biol. Chem.* 267(5) :3249–56.

Atkinson, J. B., Kitagawa, H., Humphries, B. (1992) Major surgical intervention during extracorporeal membrane oxygenation. *J. Of Pediatric Surgery* 27(9):1197–1198.

Benedict, C., Ryan, J., Wolitzky, B., Ramos, R., Gerlach, M., Tijburg, P., and Stern, D. (1991) Active site-blocked Factor Ixa prevents intravascular thrombus formation in the coronary vasculature without inhibiting extravascular coagulation in a canine thrombosis model. *J. Clin. Invest.* 88:1760–1765.

Bernabei, A., Gihahis, N., Maione, E. E., Kowalska, M. A., Yan, S., Niewiarowski, S., Edmunds, L. H., Jr. (1995) Reversal of heparin anticoagulation by recombinant platelet factor 4 and protamine sulfate in baboons during cardiopulmonary bypass. *J. Thorac. & Cardiovasc. Surg.* 109(4):765–71.

Berntorp, E., Björkman, S., Carlsson, M., Lethagen, S. and Nilsson, I. M. (1993) Biochemical and in vivo properties of high purity factor IX concentrates. *Thrombosis and Haemostasis* 70(5):768–773. Blondelle et al. (1994).

Brister, S. J., Ofosu, F. A., Heigenhauser, G. J. F, Gianese, F., and Buchanan, M. R. (1994) Is heparin the ideal anticoagulant for cardiopulmonary bypass? Dermatan Sulphate may be an alternate choice. *Thrombosis & Haemostasis* 71:468–473.

Chomiak, P. N., Walenga, J. M., Koza, M. J., Reilly, T. M., Turlapathy, P., and Pifarre, R. (1993) Investigation of a thrombin inhibitor peptide as an alternative to heparin in cardiopulmonary bypass surgery. *Circ.* 88:407–412.

Daly, R. C., McCarthy, P. M. Orszulak, T. A., Schaff, H., Edwards, I. D. (1988) Histologic comparison of experimental coronary artery bypass grafts: similarity of in situ and free internal mammary artery grafts. *J. Thorac. & Cardiovasc. Surg.* 96(1):19–29.

DeAnda, A., Coutre, S. E., Moon, M. R., Vial, C. M., Griffin, L. C., Law, V. S., Komeda, M., Leung, L. L. K., and Miller, D. C. (1994) Pilot study of the efficacy of a thrombin inhibitor for use during cardiopulmonary bypass. *Ann. Thorac. Surg.* 58:344–350.

Derian, C., VanDusen, W., Przysiecki, C., Walsh P. N., Berkner K. L., Daufman R. J., Friedman, P. A. (1989) Inhibitors of 2-ketoglutarate dependent dioxygenases block aspartyl beta-hydroxylation of recombinant human factor IX in several mammalian expression systems. *Biol. Chem.* 264:6615–6618.

Edmunds, L. H. (1993) Blood-surface interactions during cardiopulmonary bypass. *J. Card. Surg.* 8:404–410.

Edmunds, L. H. (1995) Why cardiopulmonary bypass makes patients sick: strategies to control the blood-synthetic surface interface. *Adv. In Cardiac Surg.* 6:131–167.

Freedman, S. J., Furie, B. C., Furie, B. and Baleja, J. D. (1995) Structure of the metal-free γ-carboxyglutamic acid-rich membrane binding region of factor IX by two-dimensional NMR spectroscopy. *J. Biol. Chem.* 270(14):7980–7987.

Furie, B. C. and Furie, B. (1995) Biosynthesis of factor IX: Implications for gene therapy. *Thrombosis and Haemostasis* 74(1):274–277.

Gitel, S., Stephenson, R., and Wessler, S. (1977) In vitro and in vivo correlation of clotting protease activity: effect of heparin. *Proc. Natl. Acad. Sci.* 74:3028–3032.

Gravlee, G. P., Haddon, W. S., Rothberger, H. K., Mills, S. A., Rogers, A. T., Bean, V. E., Buss, D. H., Prough, D. S., and Cordell, A. R. (1990) Heparin dosing and monitoring for cardiopulmonary bypass. *J. Thorac, Cardiovasc. Surg.* 99:518–527.

Gurewich, V., Nonn, T., and Lipinski, B. (1979) Activation of extrinsic or intrinsic blood coagulation in experimental venous thrombosis and disseminated intravascular coagulation: pathogenic differences. *Thromb. Res.* 14:931–940.

Heimark, R., and Schwartz, S. (1983) Binding of coagulation factors IX and X to the endothelial cell surface. *Biochem. Biophys. Res. Commun.* 111:723–731.

Iberti, T. J., Miller, M., Ablaos, A., Fischer, E. P., Pst, K. D., Benjamin, E., Oropello, J. M., Wiltshire-Clement, M. and Rand, J. H. (1994) Abnormal coagulation profile in brain tumor patients during surgery. *Neurosurgery* 34(3):389–395.

Keating, M. T. and Sanguinetti, M. C. (1996) Molecular genetic insights into cardiovascular disease. *Science* 272:681–685.

Kuwabara, K., Pinsky, D. J., Schmidt, A. M., Benedict, C., Brett, J., Ogawa, S., Broekman, M. J., Marcus, A. J., Sciacca, R. R., Michalak, M., Wang, F., Pan, Y. C., Grunfeld, S., Patton, S., Malinski, T., Stern, D. M. and Ryan, J. (1995) Calreticulin. an antithrombotic agent which binds to vitamin K-dependent coagulation factors, stimulates endothelial nitric oxide production, and limits thrombosis in canine coronary arteries. *J. Biol. Chem.* 270(14):8179–8187.

Lollar, P., and Fass, D. (1984) Inhibition of activated porcine Factor IX by dansyl-glutamyl-glycyl-arginyl-chloromethylketone. *Arch. Biohcem. Biophys.* 233:673–682.

London, F. And P. Walsh. (1992) *Circulation* 86:(suppl 1), 1855.

Magovern, G. L. (1995) Treatment with extracorporeal Membrane Oxygenation for Postcardiotomy Cardigenic Shock. *Advances in Cardiac Surgery* 6:169–193.

Miyata, T., Kuze, K., Matsuse, T., Komooka, H., Kamiya, K., Umeyama, H., Matsui, A., Kato, H., and Yoshioka, A. (1994) Factor IX Bm Kiryu: a Val-313-to-Asp substitution in the catalytic domain results in loss of function due to a conformational change of the surface loop: evidence obtained by chimaeric modelling. *British J. of Haematology* 88:156–165.

Muehrcke, D. D., McCarthy, P. M., Stewart, R. W., Seshagiri, S., Ogella, D. A., Foster, R. C., Cosgrove, D. M. (1995) Complications of Extracorporeal Life support systems using heparin-bound surfaces: the risk of intracardiac clot formation. *J. Thorac. Cardiovasc. Surg.* 110:843–51.

Perchinisky, M. J., Long, W. B., Hill, J. G., Parsons, J. A., Bennett, J. B. (1995) Extracorporeal Cardipulmonary Life Support with heparin bonded circuitry in the resusitation of massively injured trauma patients. *Am. J. Surg.* 169:488–491.

Rimon, S., Melame, R., Savion, N., Scott, T. Nawroth, P. P., Stern, D. M. (1987) Identification of a factor IX/IXa binding protein on endothelial cell surfaces. *J. Biol. Chem.* 262:6023–6031.

Ryan, J., Wolitzky, B., Heimer, E., Lambrose, T., Felix, A., Tam, J. P., Huang, L. H., Nawroth, P., Wilner, G., Kisiel, W., Nelsestuen, G. L., and Stern, D. M. (1989) *J. Biol. Chem.* 264:20283–20287.

Santagostino, E., Mannucci, P. M., Gringeri, A., Tagariello, G., Baudo, F., Bauer, K. A. and Rosenberg, R. D. (1994) Markers of hypercoagulability in patients with hemophilia B given repeated, large doses of factor IX concentrates during and after surgery. *Thrombosis and Haemostasis* 71(6):737–740.

Stern, D., Drillings, M., Nossel, J., Hurlet-Jensen, A., LaGamma, K., and Owen, J. (1983) Binding of factors IX and Ixa to cultured vascular endothelial cells. *Proc. Natl. Acad. Sci.* 81:913–917.

Stern, D., Knotter, G., Kisiel, W., and Nawroth, P. (1987) In vivo evidence of intravascular binding sites for coagulation factor IX. *Br. J. Hematol.* 66:227–232.

Stern, D., Nawroth, P. Kisiel, W., Vehar, G. And Esmon, D. (1985) The binding of Factor Ixa to cultured bovine endothelial cells: induction of a specific site in the presence of factor VIII and X. *J. Biol. Chem.* 260:6717–6722.

Thompson, A. (1986) Structure, function and molecular defects of Factor IX. *Blood* 67:565–572.

Toomey, J., Smith, K., and Stafford D. (1991) Localization of human tissue factor recognition determinants of human factor VIIa. *J. Biol. Chem.* 266:19198–19202.

Toomey, J., Smith, K., Roberts, H., Stafford, D. W. (1992) The endothelial binding determinent of human factor IX resides in the gamma-carboxyglutamic acid domain. *Biochemistry* 31:1086–1808.

Wacey, A. I., Krawczak, M., Kakkar, V. V. and Cooper, D. N. (1994) Determinants of the factor IX mutational spectrum in haemophilia B: an analysis of missense mutations using a multi-domain molecular model of the activated protein. *Hum. Genet.* 94:594–608.

Walenga, J. M., Bakhos, M., Messmore, H. L., Fareed, J., and Pifarre, R. (1991) Potential use of recombinant hirudin as an anticoagulant in cardiopulmonary bypass model. *Ann. Thorac. Surg.* 51:271–277.

Warrier, I., Kasper, C. K., White I. I., G. C., Shapiro, A. D., Bergman, G. E. and The Mononine® Study Group (1995) Safety of high doses of a monoclonal antibody-purified factor IX concentrate. *Am. J. of Hematol.* 49:92–94.

Wickelgren, I. (1996) New devices are helping transform coronary care. *Science* 272:668–670.

What is claimed is:

1. An assay to determine the anticoagulant activity of a Factor IXa compound on a subject's blood which comprises:

(a) mixing Factor IX deficient plasma, diatomaceous earth and plasma containing the Factor IXa compound derived from the subject's blood;

(b) incubating the resulting mixture from step (a) with an effective dose of a source of phospholipid and calcium chloride under conditions such that clot formation results; and (c) measuring the time necessary for clot formation in the incubate of step (b) so as to thereby determine the anticoagulant activity of the Factor IXa compound.

2. An assay of claim 1, further comprising comparing the time necessary for clot formation measured in step (c) with the time necessary for clot formation measured in the absence of the Factor IXa compound.

3. An assay of claim 1, wherein the subject is a human patient.

4. An assay of claim 1, wherein the Factor IXa compound is a functionally inactive form of Factor IXa.

5. An assay of claim 4, wherein the functionally inactive form of Factor IXa is a Factor IXa in which the active serine amino acid site has been altered.

6. A method for monitoring the anticoagulant activity of a Factor IXa compound infused into the circulation of a subject's blood during surgery which comprises measuring the anticoagulant activity of the Factor IXa compound at different times during the surgery using the assay of claim 23 and comparing the activities so measured.

7. A method of claim 6, wherein the subject is a human patient.

8. A method of claim 6, wherein the surgery is cardiopulmonary by pass surgery.

9. A method of claim 6, wherein the Factor IXa compound is a functionally inactive form of Factor IXa.

10. A method of claim 9, wherein the functionally inactive form of Factor IXa is a Factor IXa in which the active serine amino acid site has been altered.

* * * * *